United States Patent [19]

Zeilinski et al.

[11] Patent Number: 5,012,817
[45] Date of Patent: May 7, 1991

[54] DOLORIMETER APPARATUS

[75] Inventors: Adam Zeilinski; Christopher J. Atkins, both of Victoria, Canada

[73] Assignee: University of Victoria, Victoria, Canada

[21] Appl. No.: 354,370

[22] Filed: May 19, 1989

[51] Int. Cl.$^5$ ............................................. A61B 5/22
[52] U.S. Cl. .................................... 128/744; 128/774
[58] Field of Search ....................... 128/744, 774, 782

[56] References Cited

U.S. PATENT DOCUMENTS

| | | | |
|---|---|---|---|
| 4,144,877 | 3/1979 | Frei et al. ............................ | 128/774 |
| 4,501,148 | 2/1985 | Nicholas et al. . | |
| 4,503,705 | 3/1985 | Polchaninoff ................... | 128/774 X |
| 4,641,661 | 2/1987 | Kalarickal ........................... | 128/744 |
| 4,768,521 | 9/1988 | Schiffman et al. .................. | 128/774 |

FOREIGN PATENT DOCUMENTS 516026 6/1979 Australia .
158336 10/1985 European Pat. Off. .
8708251 8/1987 Fed. Rep. of Germany .

OTHER PUBLICATIONS

Proceedings of the Ninth Annual Conference of the I.E.E.E. Engineering in Medicine and Biology Science—Nov. 13–1987.

*Primary Examiner*—Lee S. Cohen
*Assistant Examiner*—K. M. Pfaffle
*Attorney, Agent, or Firm*—Shlesinger & Myers

[57] ABSTRACT

A dolorimeter apparatus comprises a member having a property which varies according to pressure applied to the member. A device is provided for securing the member to a hand of a user so the member fits under a finger of the user. The member is dimensioned to fit between the finger and an object touched by the user while permitting substantial tactile communication to the finger. A device is provided for quantifying the variance in said property from said member.

19 Claims, 2 Drawing Sheets

DOLORIMETER APPARATUS

BACKGROUND OF THE INVENTION

This invention relates to an apparatus for measuring the minimum pressure applied to a patient which elicits discomfort, for example the pressure applied to a joint of an arthritic patient.

Physicians place an important role on patterns of pain in the diagnosis and management of their patients. Manual palpitation is the standard method of examination, but it has a certain drawback, namely that the procedure is subjective and lacks the precision necessary to accurately assess, for example, the degree of inflammation of arthritic patients.

The limitations of manual palpitation have been addressed by providing mechanical devices known as dolorimeters, algesimeters or algometers (the terms are used synonymously herein). In the simplest form, a mechanical dolorimeter includes a simple spring loaded probe connected to a gauge. The gauge indicates the deflection of the probe and hence the pressure applied to the probe. In use, the physician presses the probe against the inflamed joint or other portion of the patient's body suffering pain, and applies pressure until the patient feels discomfort. The reading of the gauge is noted, the reading being an objective indication of the degree of inflammation of the joint, for example.

Electronic dolorimeters have been developed, such as disclosed in U.S. Pat. No. 4,641,661 to Kalarickal. This device includes an electronic circuit housed in a hand-held unit. The dolorimeter has a probe with a resistance which varies according to pressure applied to the probe. The hand-held unit is capable of measuring the resistance of the probe and thereby the pressure applied.

Other devices for determining or recording the pain sensitivity or the like are disclosed in U.S. Pat. No. 4,501,148 to Nicholas, U.S.S.R. Patent No. 166,999, Federal German Patent No. 230,696 and European Patent No. 158,336 to Wood.

All of the devices described above substitute the finger of the physician with an inanimate probe. For this reason, they have an inherent drawback in that they remove certain advantages to the physician and the patient inherent in the touch of the physician's finger. The physician's finger is capable of determining with accuracy the precise point where the pain threshold is to be assessed. It is not always easy for the physician to press the inanimate probe at precisely the right location because he or she receives no direct tactile feedback from the probe. In addition, there is an impersonal aspect objectionable to some patients associated with the act of being pressed with an inanimate object. Many patients would prefer the more personal contact of a physician's finger.

It is therefore an object of the invention to provide a dolorimeter apparatus which can output a objective reading of the minimum pressure which causes discomfort and the beneficial aspects of manual palpitation.

SUMMARY OF THE INVENTION

The invention provides a dolorimeter apparatus having a member with a property, such as electrical resistance, which varies according to pressure applied to the member. There is means for securing the member to a hand of a user so the member fits under a finger of the user. The member is dimensioned to fit between the finger and an object touched by the user while permitting substantial tactile communication to the finger. There is means for quantifying the variance in the property from said member. For example, the member may include a pressure sensitive film deposited on a flexible substrate.

The apparatus may also include means for receiving information relating to the quantified variance of the property of the member and for displaying a value indicative of said property and thereby the pressure applied to the member. The means for receiving and displaying may include a ohmmeter.

DESCRIPTION OF THE PREFERRED EMBODIMENT

Figure 1:
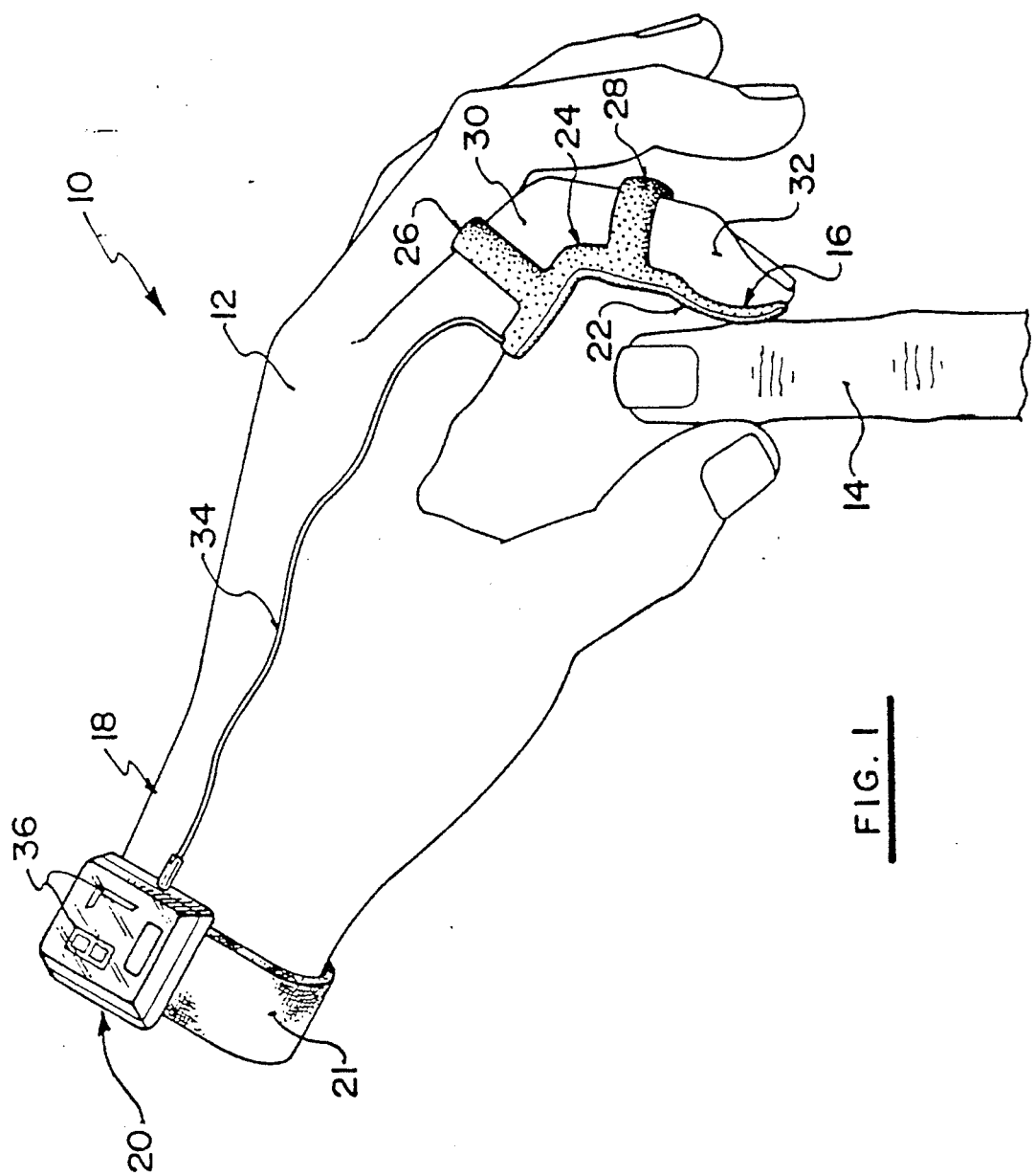
FIG. 1 is a perspective view showing a dolorimeter apparatus including a pressure sensitive member secured to a finger of a user, a unit mounted on the wrist of the user for receiving a signal from the pressure sensitive member and for displaying indicia representing said pressure and a finger of a patient.

Referring to FIG. 1, a dolorimeter apparatus is shown generally at 10 in association with a physician's hand 12 and a finger 14 of a patient. The apparatus has two principal components, namely a pressure responsive member 16 having a property which varies according to pressure applied to the member and a receiving and display apparatus 20, in this preferred example mounted on wrist 18 of the physician.

Referring firstly to the pressure responsive member 16, the member includes a pressure sensitive film 22 on a flexible, sheet-like substrate 24. In the preferred embodiment, the film 22 is a shunt-mode force sensing resistor of the type sold by Interlink Electronics of Santa Barbara California, U.S.A. Force sensing resistors as supplied by the said company are in accordance with one or more of the following U.S. Pat. Nos: 4,451,714; 4,276,538; 4,314,228; 4,301,337; take disclosure of which are incorporated herein by reference. This device has an electrical resistivity which varies according to the pressure applied to the film. The film is mounted on a substrate which may be, for example, a relatively thin elastomeric membrane having contacts printed thereon for contacting the film 22. The member further includes means for securing the member to the physician's hand which comprises a pair of bands 26 and 28 in this embodiment, the bands being shaped to fit about index finger 30 of the physician. When fitted in place, the film 22 is under tip 32 of the index finger.

The apparatus includes means for outputting a signal representing the property of the member which varies with pressure applied to the member, in this case the resistivity of the film. In this embodiment the means for outputting includes a 2-wire electrical conductor 34 which is connected to the contacts contacting the film 22 at one end and to receiving and display apparatus 20 at the other end.

The receiving and display apparatus in its simplest form can be an ohmmeter with digital display 36 on the face thereof for indicating the instantaneous resistance of the film. Such ohmmeters are well known and thus an additional description is not provided. The indicia can simply be a numerical representation, for example on a liquid crystal display, of the resistance of the film. Preferably, however, the apparatus 20 includes a circuit for converting the resistance value to a number in units meaningful to the physician indicative of the pressure applied to finger 14 such as psi or new units unique to this instrument. In the preferred embodiment the apparatus 20 is connected to a wrist strap 21 which can be worn on the wrist of a user such as a physician.

Figure 2:
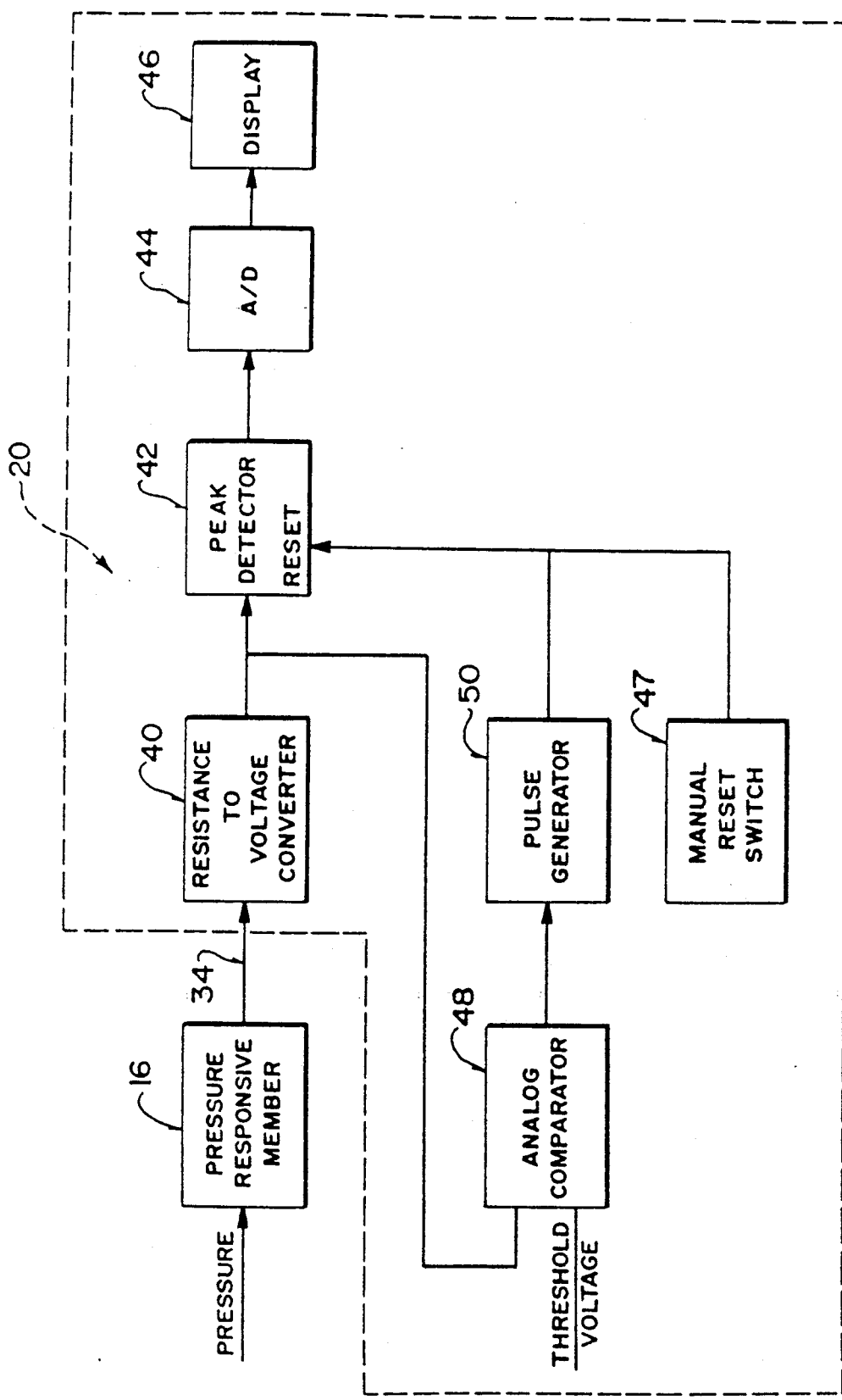
FIG. 2 is a block diagram of the dolorimeter apparatus.

Referring to FIG. 2, in the preferred embodiment the pressure responsive member 16 is connected by electrical conductor 34 to a resistance-to-voltage converter 40 of the display apparatus shown in broken outline generally at 20. The resistance-to-voltage converter provides an output voltage signal representing resistance measured at the pressure responsive member and therefore ultimately represents the pressure applied to the member.

The output of the resistance-to-voltage converter is supplied to a peak detector 42. The peak detector monitors the output voltage from the resistance-to-voltage converter. The peak detector provides its own output voltage which tracks the output voltage of the resistance-to-voltage converter until a highest value is attained, at which time the output voltage of the peak detector is held at this highest value. The output voltage from the peak detector is supplied to an analog-to-digital converter 44 where it is converted into a digital format. The digital format is supplied to an output device such as a digital display 36 which displays data representing pressure applied at the pressure responsive member.

The display device has two modes of operation, one in which the device is manually reset and a second in which the device is automatically reset. In the manual reset mode, a simple switch 47 is provided to reset the peak detector 42 after a pressure measurement is taken. To use the device in this mode, a physician applies pressure to a patient's finger using the pressure responsive member 16. As the physician gradually increases pressure on the finger, the output voltage of the resistance-to-voltage converter 40 is monitored by the peak detector 42 and pressure values are seen to increase at the digital display 46. At the onset of pain indicated by the patient, the physician may release the pressure from the finger at which time the peak detector 42 will retain at its output the voltage representing the highest pressure inflicted or, in other words, the pain threshold of the patient. The pain threshold pressure value will be displayed on the digital display 36. The display 36 will continue to indicate this pressure value until the physician actuates the manual reset switch thereby resetting the peak detector 42. Resetting the peak detector 42 sets the display 36 back to zero. The apparatus is thus rendered ready to take another pressure measurement.

In the automatic reset mode, the output of the resistance-to-voltage converter is supplied to an analog comparator 48. The comparator compares this voltage with a threshold voltage and causes the output of the comparator to change the state of its output when the threshold value is exceeded. The output of the comparator is connected to a pulse generator 50 which detects the change in state of the comparator and generates a pulse of short duration. The pulse is supplied to the peak detector 42 and serves to reset the peak detector when the voltage from the resistance-to-voltage converter crosses the threshold level at the comparator. Typically, the threshold level at the comparator is set to a value lower than the minimum voltage output of the resistance-to-voltage converter for a minimum pressure reading taken by the physician.

In operation, in the automatic reset mode, the physician gradually applies pressure to the finger of the patient thereby changing the resistance of the pressure responsive member and causing the output of the resistance-to-voltage converter 40 to increase. Upon application of minimal pressure, the output voltage of the resistance-to-voltage converter 40 exceeds the threshold voltage at the comparator and causes the comparator output to change state. This change of state is detected by the pulse generator 50 which resets the peak detector 42. The peak detector 42 is thus rendered ready to track and monitor the output of the resistance-to-voltage converter. The digital display 36 continuously displays the changing output voltage of the peak detector as the pressure at the patient's finger is increased.

At the onset of pain indicated by the patient, the physician releases the pressure on the patient's finger and the peak detector maintains its output voltage at a value representing the greatest pressure applied to the patient. A numerical value representing this pressure is indicated in appropriate units and maintained on the display even after the physician has released the pressure on the patient's finger. The numerical value will continue to be displayed until pressure is again applied to the pressure responsive member. It may readily be seen that when using the device in the automatic mode, the physician need not press the manual reset button and therefore the device can be easily operated with one hand only. Use of the device in the automatic reset mode also appreciably reduces examination time.

Other means could be used for receiving and displaying the value indicative of the pressure applied to the finger. For example, a Wheatstone bridge can be used to determine the resistance of the film. In addition, the member 16 can have other variable properties depending upon the pressure. Potentially a piezoelectric device could be used and the means for receiving and displaying could indicate the voltage output of the piezoelectric device. A member with a variable capacitance property is another possibility. Such a sensor can be formed by depositing thin conducting layers on both sides of a thin elastomeric substrate. A pressure applied to such material will change its thickness and therefore capacitance of the sensor. Changes of capacitance can be sensed by a variety of well known methods such as an ac bridge, or a variable frequency oscillator.

The member 16, and in particular the portion under the finger tip 32 is sized so as to permit substantial tactile communication to the physician's finger when touching an object, such as the joint of the patient's finger 14. In this preferred embodiment the tactile communication is achieved by making the film and the substrate relatively thin to accommodate the sense of the touch of the physician. Other possibilities include providing a thin substrate with a very small, but rigid pressure sensitive unit which would be relatively unobtrusive and, again, permit a substantial tactile communication between the physician and the patient's afflicted joint for example.

In another version of the invention, there is a communications ability between receiving and display apparatus 20 and a computer to record measured data. A short range telemetry link, such as an infrared beam similar to that used for T.V. controls, can be employed.

While specific embodiments of the invention have been described, such embodiments should not be considered as limiting the scope of the invention as construed in accordance with the accompanying claims.

What is claimed is:

1. A dolorimeter apparatus comprising:
a member having an electrical property which varies according to pressure applied to the member, means for securing the member to a hand of the user so said member fits under a finger tip of the user, the member comprising a pressure sensitive flexible film dimensioned to fit between the finger tip and body tissue to be touched by the user, the member being sufficiently thin and flexible to permit substantial tactile communication between said finger and the body tissue to enable the user to monitor manually the application and location of force applied to the body tissue, and means connected to the member for quantifying the variance in said property outputted from said member.

2. An apparatus as claimed in claim 1, wherein the film is on a flexible substrate.

3. An apparatus as claimed in claim 1, wherein said property is electrical resistance of the film.

4. An apparatus as claimed in claim 1, wherein said property is capacitance.

5. An apparatus as claimed in claim 1, wherein the means for securing the member includes a band connected to the member, the band having a size to pass around the finger.

6. An apparatus as claimed in claim 1, further including an electrical conductor extending between the member and the means for quantifying the variance in said property outputted from said member.

7. An apparatus as claimed in claim 1 wherein the means for quantifying the variance in said property of said member includes electronic circuit means for providing a signal representing the pressure applied to the member.

8. An apparatus as claimed in claim 7 wherein said electronic circuit means includes means for tracking said signal and for holding automatically said signal in a state representing a highest value of pressure applied to the member.

9. An apparatus as claimed in claim 8 wherein the means for tracking and holding is reset when said signal crosses a threshold value.

10. An apparatus as claimed in claim 8 wherein said electronic circuit means includes an output device for indicating pressure applied to the member.

11. An apparatus as claimed in claim 10 wherein said output device includes a digital display.

12. A dolorimeter apparatus, comprising:
a flexible member having electrical resistance which varies with pressure applied to the member, the member comprising a pressure sensitive flexible film dimensioned to fit between a finger tip of a user and body tissue to be touched by the user, the member being sufficiently thin and flexible to permit substantial tactile communication between said finger and the body tissue to enable the user to monitor manually the application and location of force supplied to the body tissue;
means for securing the member under the finger tip of the user of the apparatus;
means electrically connected to the member for outputting a signal indicating the electrical resistance of the member;
means for receiving said signal and for displaying a value inndicative of said electrical resistance of the member and thereby the pressure applied to the member.

13. An apparatus as claimed in claim 12 wherein said means for receiving and for displaying includes electronic circuit means for providing a signal representing the pressure applied to the member.

14. An apparatus as claimed in claim 13 wherein said electronic circuit means includes means for tracking said signal and for holding automatically said signal in a state representing a highest value of pressure applied to the member.

15. Ann apparatus as claimed in claim 14, wherein the means for tracking and holding is reset when said signal crosses a threshold value.

16. An apparatus as claimed in claim 13, wherein the means for receiving and displaying includes an ohmmeter.

17. An apparatus as claimed in claim 13, wherein the means for receiving and displaying includes a wrist strap so the means for receiving and displaying can be worn on the wrist of a user.

18. An apparatus as claimed in claim 12, wherein the means for outputting includes electrical wires operatively connected to the member and to the means for receiving and displaying.

19. An apparatus as claimed inn claim 13, wherein the pressure sensitive film on is supported a flexible substrate.

* * * * *

UNITED STATES PATENT AND TRADEMARK OFFICE
CERTIFICATE OF CORRECTION

PATENT NO. : 5,012,817

DATED : May 7, 1991

INVENTOR(S) : Adam Zielinski et al

It is certified that error appears in the above-identified patent and that said Letters Patent is hereby corrected as shown below:

Title page, item [75] Inventor:
The inventor identified as Adam Zeilinski should be identified as Adam Zielinski.

In column 1, at lines 11 and 16, delete "palpitation" and substitute -- palpation -- therefor.

In column 6, at line 32, change "Ann" to --An--; at line 47, delete "on"; and at line 47, between "supported" and "a" insert --by--.

Signed and Sealed this

Twentieth Day of July, 1993

*Attest:*

MICHAEL K. KIRK

*Attesting Officer*  Acting Commissioner of Patents and Trademarks